(12) United States Patent
Hauke

(10) Patent No.: US 9,251,403 B2
(45) Date of Patent: Feb. 2, 2016

(54) METHOD FOR FINDING AND DIGITALLY EVALUATING ILLEGAL IMAGE MATERIAL

(71) Applicant: ATG Advanced Swiss Technology Group AG, Pfaeffikon (CH)

(72) Inventor: Rudolf Hauke, Kreuzlingen (CH)

(73) Assignee: ATG Advanced Swiss Technology Group AG, Pfaeffikon (CH)

( * ) Notice: Subject to any disclaimer, the term of this patent is extended or adjusted under 35 U.S.C. 154(b) by 117 days.

(21) Appl. No.: 13/792,840

(22) Filed: Mar. 11, 2013

(65) Prior Publication Data

US 2013/0188842 A1 Jul. 25, 2013

Related U.S. Application Data

(63) Continuation of application No. PCT/EP2010/063276, filed on Sep. 10, 2010.

(51) Int. Cl.
 *G06K 9/00* (2006.01)
 *G06Q 10/10* (2012.01)
 *A61B 5/117* (2006.01)

(52) U.S. Cl.
 CPC ........ *G06K 9/00288* (2013.01); *G06K 9/00718* (2013.01); *G06Q 10/10* (2013.01); *A61B 5/117* (2013.01); *A61B 5/1176* (2013.01); *A61B 5/1178* (2013.01)

(58) Field of Classification Search
 None
 See application file for complete search history.

(56) References Cited

U.S. PATENT DOCUMENTS

| | | | |
|---|---|---|---|
| 7,765,309 B2* | 7/2010 | Spearman et al. | 709/229 |
| 8,825,518 B2* | 9/2014 | Levy | 705/14.26 |
| 2003/0012399 A1* | 1/2003 | Wu | 382/100 |
| 2007/0085710 A1* | 4/2007 | Bousquet | G06F 17/30539 341/50 |
| 2008/0159624 A1* | 7/2008 | Sathish et al. | 382/170 |
| 2009/0123064 A1* | 5/2009 | Gibbs | 382/165 |
| 2009/0248696 A1* | 10/2009 | Rowles et al. | 707/10 |
| 2010/0125502 A1* | 5/2010 | Solomon et al. | 705/14.52 |
| 2010/0299453 A1* | 11/2010 | Fox et al. | 709/246 |
| 2012/0259890 A1* | 10/2012 | Denesuk et al. | 707/776 |
| 2014/0259097 A1* | 9/2014 | Brock et al. | 726/1 |

OTHER PUBLICATIONS

Association of Chief Police Officers by the National Centre for Policing Excellence, "Practice Advice on Investigating Indecent Images of Children on the Internet," at http://www.kent.police.uk/about_us/policies/n/documents/n85_acpo.pdf (2005).

Carr, "Childbase Child Protection and Recovery Software," Round Table on Respect of the Rights of the Child on the Internet, found at http://xuk.obu-investigators.com/pdf/JohnCarrParis2003.pdf (Nov. 20, 2003).

(Continued)

*Primary Examiner* — Vikkram Bali

(74) *Attorney, Agent, or Firm* — Muncy, Geissler, Olds & Lowe, P.C.

(57) ABSTRACT

A method for finding and digitally evaluating illegal image material is provided, wherein a data memory is searched for image material. Image material that is found is classified as potentially illegal image material or as legal image material by means of a classification method on the basis of an image content that is presented. The image material graded as potentially illegal has the age of the persons shown determined, and potentially illegal image material which shows at least one person whose ascertained age is below a prescribed age is graded as illegal image material. Biometric features of the persons shown in the illegal image material are detected and are compared with at least one database which contains biometric features. In the illegal image material, at least one further feature which it contains is detected and is compared with at least one appropriate database.

17 Claims, 1 Drawing Sheet

(56) References Cited

OTHER PUBLICATIONS

Garcia et al., "Image and Video Processing Survey, FIVES Forensic Image and Video Examination Support," http://fives.kau.se/uploads/Results/SurveyReport.pdf (Feb. 1, 2010).

FIVES consortium, "SIP-2008-TP131801, FIVES, Annual Report Feb. 1, 2009-Jan. 31, 2010," http://fives.kau.se/uploads/Results/AnnualReport.pdf (Feb. 1, 2010).

Lienhart et al., "Filtering Adult Image Content with Topic Models," IEEE Conf. on Multimedia and Expo 2009, pp. 1472-1475 (Jun. 28, 2009).

* cited by examiner

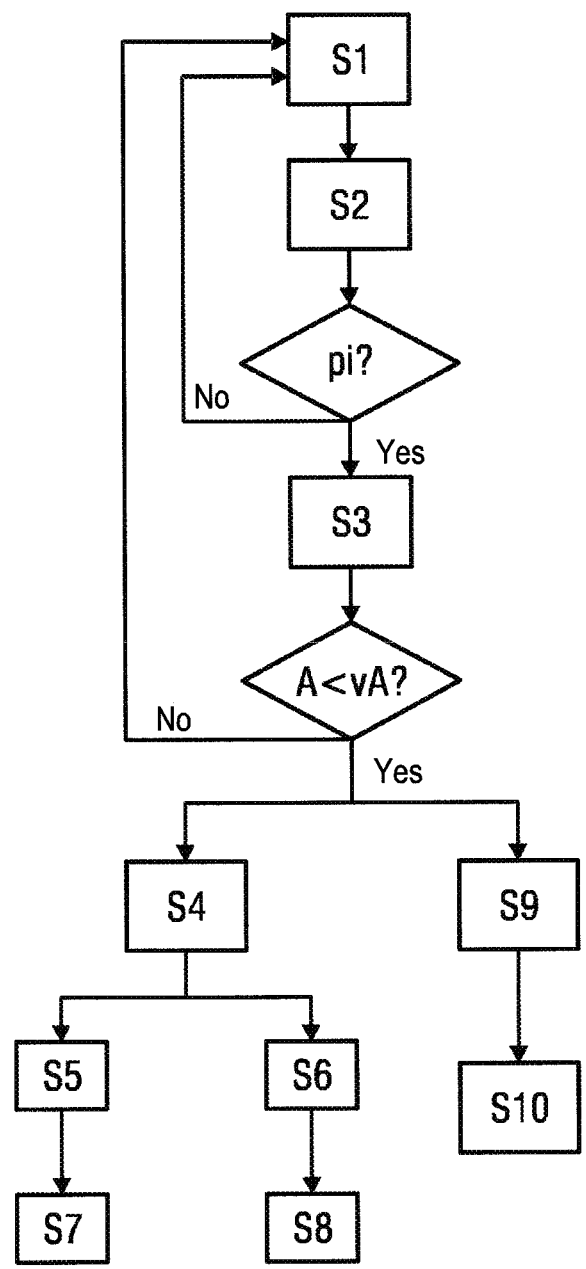

US 9,251,403 B2

METHOD FOR FINDING AND DIGITALLY EVALUATING ILLEGAL IMAGE MATERIAL

This nonprovisional application is a continuation of International Application No. PCT/EP2010/063276, which was filed on Sep. 10, 2010, and which is herein incorporated by reference.

BACKGROUND OF THE INVENTION

1. Field of the Invention

The invention relates to a method for finding and digitally evaluating illegal image material.

2. Description of the Background Art

Searching through data memories for digital image material, evaluating the found image material digitally, and filtering it based on its content are known from the conventional art. In this regard, the image material to be evaluated can be single images and also image sequences in the form of films. This makes it possible, for example, for law enforcement agencies to analyze data memories of suspects in regard to illegal image material, for example, image material of sexual child abuse.

During the digital evaluation of the found image material, the image material is encoded by means of cryptographic hash functions and compared with cryptographic hash values of already known clearly illegal image material in relevant databases. If the cryptographic hash values match, then the image material found in the data memory is clearly illegal.

To find not yet captured illegal image material, the image material found in the data memory must be evaluated by visual inspection by individuals from law enforcement agencies. This relates to both completely new and also only slightly changed image material, already known per se, because the cryptographic hash values of the image material are changed even by a minor change in it and therefore no longer match the corresponding comparative image material or its cryptographic hash values in the databases. It is therefore not possible to digitally evaluate such new or changed image material to determine whether it is illegal image material.

SUMMARY OF THE INVENTION

It is therefore an object of the invention to provide an improved method for finding and digitally evaluating illegal image material.

In an embodiment for finding and digitally evaluating illegal image material, a data memory is searched for image material.

According to an embodiment of the invention, found image material is classified by means of a classification method based on a depicted image content as potentially illegal image material or as legal image material. For example, the method of "probabilistic latent semantic analysis (PLSA) is used as a classification method for classifying the image material. Its use is described, for example, in the article" FILTERING ADULT IMAGE CONTENT WITH TOPIC MODELS" by Rudolf Hauke and Rainer Lienhart (Lienhart, R. and Hauke, R. 2009; Filtering adult image content with topic models; in *Proceedings of the* 2009 *IEEE International Conference on Multimedia and Expo* (New York, N.Y., USA, Jun. 28-Jul. 3, 2009); IEEE Press, Piscataway, N.J., 1472-1475.). Alternatively or in addition, film sequences in particular with a plurality of single images can be classified as potentially illegal image material, i.e., as image material with a sexually explicit content, also based on shown characteristic movement sequences of sexual acts by the persons shown in the image material, particularly based on such characteristic movement sequences of individual body regions of the depicted persons, and/or audio material, belonging to the film sequence, with sounds, noises, and language elements characteristic for sexual acts.

According to an embodiment of the invention an age determination of the depicted persons is carried out in the image material classified as potentially illegal, and potentially illegal image material that shows at least one person whose determined age falls below a predetermined age is classified as illegal image material. Furthermore, according to the invention biometric features of the persons shown in the illegal image material are detected and compared with at least one database containing biometric features. Moreover, according to the invention at least one contained additional feature is detected in the illegal image material and compared with at least one relevant database.

The method for finding and digitally evaluating illegal image material enables an effective automatic search for illegal image material, particularly also for new or changed image material that would not be found by methods according to the state of the art, functioning exclusively with encoding of the image material, for example, by a cryptographic hash function or a plurality of cryptographic hash functions and a comparison of the encoding. In this regard, the method has a very high accuracy based on the classification of the image material by means of a classification method and the additional age determination of the depicted persons. This enables in particular efficient searching in very large databases. A personal visual inspection of each individual image material found in the particular data memory is not necessary because of the automatic search and evaluation of the image material.

Furthermore, the detection of biometric features of the depicted persons and the comparison of the determined biometric features with one or more relevant databases enables identification of the depicted victims and offenders. Such databases for identifying offenders are, for example, databases of registered sex offenders or other available databases with biometric features, in the USA, for example, social services databases. Databases for identifying victims are, for example, missing children databases or databases with school year photos. Further, searches for image material can be carried out by means of biometric features worldwide via the Internet, computer, and server in order to remove it.

The identification of victims and offenders and the identification of the crime site by determining other features in the image material make it possible in particular to find the victims and offenders and in this way to stop the sexual abuse of children and the sexual abuse of other children by the offenders. Physical and psychological injuries and disorders in the victims are prevented in this way, at least once they have been found. Apart from the destroyed or at least greatly disturbed life of the victims, considerable social and economic damage is also associated with such inquiries, especially also psychological injuries and damage to the victims, which often persist for the entire life of the victims, because the victims often cannot pursue a normal life, i.e., a normal family life and a normal working life, and require intensive psychological care. Therefore, it is especially important to find the victims early to end the sexual abuse and further to find the offenders early to prevent sexual abuse of other victims from the start. The method makes a considerable contribution to this.

The age determination is made, for example, based on physical features, preferably based on the face of the specific person shown.

The method can be used both for finding and digitally evaluating single images and also of films; i.e., the term "image material" is to be understood as both single images and also as films, consisting of a plurality of single images, in digital form. Further, the term "image material" is also to be understood as three-dimensional image material, three-dimensional depictions, and three-dimensional representations, also called avatars, for example, produced with the use of body scans of the depicted persons.

In an embodiment of the invention, the avatar of the three-dimensional model of the specific person shown in the three-dimensional image material can also be used to generate a variety of projections of the body of the person, shown three-dimensionally, in two-dimensional images; i.e., two-dimensional depictions from different perspectives are generated from the three-dimensional depiction of the person, for example, from the front and side. The two-dimensional depictions generated in this way can then be used to search relevant databases, particularly databases with biometric features and image databases, which are still based according to the state of the art on two-dimensional depictions of persons, in order to find the depicted persons in the databases in this way.

Because only depictions of real underage persons are evaluated as child abuse, it must be verified expediently between the finding of the image material in the data memory and the detection of biometric and other features whether the image material shows real people or whether it is drawn image material or image material produced by special effects in some other manner or animated image material, for example, an animated film, a computer-generated animation film, or a so-called anime. Naturally also no biometric features of real persons can be detected or other features of a real crime site detected in such drawn image material or image material produced by special effects. Image material depicting real persons is to be differentiated from such drawn image material or image material produced by special effects or animated image material based on its properties, because drawn image material or image material produced by special effects in some other manner or animated image material in contrast to image material depicting real persons in a real environment has no noise and no blurring due to camera shake and different color depths than image material of real persons and real backgrounds. This can be determined with suitable methods, for example, with methods for color analysis or color histogram analysis.

The age below which the persons depicted in the image material need to be in order to classify the image material as illegal image material can be predetermined preferably by a user of the method, i.e., for example, by specific law enforcement agencies, because the particular age at which an act or depiction is classified as sexual child abuse is different worldwide.

Body size, at least one fingerprint, facial geometry, hand vascular pattern, vein pattern, hand geometry, palm line pattern, nailbed pattern, ear shape, voice, speech, at least one lip movement, gait, movement sequence, a skin characteristic, skin pore pattern, skin color, hair color, at least one sexual characteristic, dental status, at least one feature of at least one article of clothing, at least one body modification, and/or a feature of an iris and/or retina are detected expediently as a biometric feature of the particular depicted person.

Preferably all biometric features detectable in the particular image material are used, whereby various known methods, for example, for fingerprint detection in single images, image sequences, and three-dimensional representations, and methods for facial recognition, voice recognition, iris recognition, and recognition of lip movements are available for detection of the individual biometric features. Of course, however, methods developed in the future can also be used for this. Biometric features can be readily extracted especially in image sequences, i.e., in a film with a plurality of single images, in which persons are depicted, for example, from different perspectives. It is known, for example, to derive a biometric feature from a number of profile images of the head of a person shown from different perspectives or to determine a three-dimensional image of a face or complete head of the depicted person from a number of such profile images. It is also especially readily possible to extract biometric features of the depicted person from three-dimensional image material.

The country or the part of the world from which the persons came can be determined, for example, by analyzing speech. Furthermore, analysis of speech and voice offers another possibility for the age recognition of the depicted persons. The skin characteristics also include, for example, birthmarks, moles, scars, and other skin features or skin lesions. Characteristic features of articles of clothing can also be determined as a biometric feature in a broader sense. Such biometric features are often listed in databases, for example, in missing children databases or in databases for identifying offenders, so that a very good comparison and a good identification are possible. For example, articles of clothing that the children last wore are often also included in missing children databases. Body modifications are understood to be all voluntary or required visible changes on the body of the depicted persons, for example, scars, tattoos, piercings, transdermal implants, scarifications, or amputations.

Preferably information on a recording place and/or recording time of the image material is detected as an additional feature contained in illegal image material. Position data, which were determined by a recording device for recording the image material by means of a global positioning system and stored together with image data of the image material, are detected especially preferably as information on the recording place for the image material. For example, a plurality of recording devices, i.e., photo and video cameras, have a receiver for signals of the satellite-supported global positioning system, so that they constantly detect their current position and store it together with the image data. In this way, crime sites of the depicted acts can be determined in a simple way, as a result of which finding offenders and victims is also made easier.

At least one section of a surrounding area shown in the image material, at least one depicted object, at least one window, at least one door, at least one distinguishing feature of at least one depicted product, at least one reflective surface, and/or a characteristic of at least one wall, a floor, and/or a ceiling are detected expediently as an additional feature in the illegal image material. This is used in identifying or at least localizing the shown crime site, for example, by identifying objects such as furniture or other objects or products, for example, based on recognizable logos or trademarks, which are not obtainable globally or not obtainable globally in the shown form, but only in certain parts of the world.

Furthermore, for example, at least one painting, at least one poster, and/or at least one clock can be detected as an additional feature. A clock based on its shape and design can provide information on the crime site or at least the region of the world where the crime site is located. Furthermore, the time when the image was taken can be determined on a shown clock and, if the clock has a date display, a date when it was taken as well. A painting, which as an original or reproduction is at least relatively rare, can provide an indication of the crime site, the region of the crime site, or the owner of the painting. This also applies to posters, for example, of known personalities or places or local conditions. Such posters are often distributed only in locally limited areas of the world, so that the part of the world where the shown crime site is located can be at least concluded from them. This is also possible, for example, based on a wall, floor, or ceiling design, for example, based on characteristic wallpaper. Furthermore, the determined features can also be compared with features determined from other image material. If the crime site was already determined, for example, from other image material and has been identified, but the persons shown in the currently analyzed image material are not yet known, their identification is made easier by the knowledge of the crime site and its localization.

Shown crime sites can also be compared by the recognition of windows and doors. In addition, wider surroundings of the crime site and thereby also the crime site itself can be identified, for example, based on visible characteristic features of the surrounding area particularly through windows or through open doors, for example, characteristic buildings, or at least a region of the world where the crime site could be located can be narrowed down, for example, based on the weather situation, for example, snowfall, visible through windows or doors. When reflective, i.e., mirror-like surfaces are detected, for example, other characteristic features can be detected on these surfaces, for example, additional features of the surroundings and biometric features of persons reflected on the reflective surfaces.

If the illegal image material is a film comprising a plurality of single images, a plot is expediently detected as an additional feature present in the illegal image material. In this way, the image material can be compared with already known image material, in which the crime site, offender, and/or victim may already have been identified.

In an embodiment, a unique identifier is generated for each found illegal image material. This unique identifier is, for example, a cryptographic hash function or some other identifier used to search for illegal image material with methods according to the state of the art.

Expediently, the generated unique identifier is entered in at least one database, preferably in all existing databases with such identifiers. In this way, users of other methods searching for illegal image material based on such identifiers, can use these identifiers and also find this new image material. This facilitates the work of law enforcement agencies and police authorities, which generally are the users of these other methods.

In an embodiment, an age adjustment of the detected biometric features according to at least one predetermined age is carried out and determined age-adjusted biometric features are compared with at least one database containing biometric features. The age is preferably predetermined by the user of the method. In this way, for example, offenders and victims can be identified who are depicted in the new image material and whose biometric data in the databases are already several years old, for example, children who have been missing for years. Some of the biometric data are subjected to changes during the aging process, for example, body size.

If, for example, the date on which the image material was recorded is known, by age adjustment of the detected biometric features by a few years searches can be run in databases of missing children, who have already been missing for years, for example, with the age-adjusted biometric features, and victims can be identified in this way. Methods are known, for example, which extrapolate the aging process of a face. For example, the appearance of a face of an 8-year-old victim can be projected to the current date in this way, or the appearance of a currently depicted victim can be projected to a date when the victim perhaps disappeared. As a result, recovery by means of facial recognition is greatly improved. This applies in a similar way to the identification of offenders, because the data material in many databases is often not current. Nevertheless, because of the older age of the offenders, changes in biometric features are often minor here and relate, for example, to a change in hair color or to changes on a face, for example, an increase in wrinkles.

As a data memory, for example, a permanently installed or mobile memory unit of a permanently installed or mobile computer, a database server, a mobile telephone, or some other permanently installed or mobile device, for example, also servers of a social network database or a so-called cloud is searched. Any data memory in any type of devices can be searched by means of the method, for example, also data memories far removed from the particular end devices, for example, servers which can be reached by data communication, for example, over the Internet. This will increase further in the future by so-called cloud computing, so that the actual end devices no longer have their own data memories.

In an embodiment, in addition to the search for image material, the data memory is also searched for access data, for example, in files of electronic messages, i.e., email, or in text files. Found access data also enable and facilitate the search for image material in other data memories, which can be accessed by the owner of the particular end device or data memory. Moreover, by means of such access data, for example, access to file-sharing sites, chat rooms, and other platforms is made possible, in which, for example, illegal image material is offered, traded, and/or exchanged or other illegal activities occur. Furthermore, the indirect possession of illegal data is also already prohibited in the majority of international laws; i.e., the possession of access data, which enable access to illegal image material, is also already prohibited.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The present invention will become more fully understood from the detailed description given hereinbelow and the accompanying drawing which is given by way of illustration only, and thus, is not limitive of the present invention, and wherein the sole FIGURE illustrates an example embodiment, showing a cross-sectional view of an adjustment fitting with sealing of the eccentric receiving space, and wherein the FIGURE shows a schematic illustration of a process sequence.

DETAILED DESCRIPTION

FIG. 1 shows a schematic illustration of an embodiment of a process sequence of a method for finding and digitally evaluating illegal image material, particularly image material on sexual child abuse. In the method, in a first process step S1 a data memory is searched for image material.

The data memory can be, for example, a permanently installed or mobile memory unit of a permanently installed or mobile computer, a database server, a mobile telephone, or some other permanently installed or mobile device. Any data memory in any type of devices can be searched by means of the method, for example, also data memories far removed from the particular end devices, for example, servers which can be reached by data communication, for example, over the Internet. This will increase further in the future by so-called cloud computing, so that the actual end devices no longer have their own data memories.

The image material for which the data memory is searched and which is digitally evaluated in the further process sequence can be both single images and also films; i.e., the term image material is understood to be both single images and films, consisting of a plurality of single images, in digital form. Further, the term "image material" is also to be understood as three-dimensional image material, three-dimensional depictions, and three-dimensional representations, for example, produced with the use of body scans of the persons shown.

If image material is found, for example, an image file or video film file, in a second process step S2 a search is run for the persons depicted in the image material and these persons are detected and a search is run particularly for sexually explicit depictions of persons. To this end, the found image material is classified by means of a classification method based on a depicted image content as potentially illegal image material pi, i.e., as image material with a sexually explicit content, or as legal image material. For example, the method of "probabilistic latent semantic analysis (PLSA) is used as a classification method for classifying the image material. Its use is described, for example, in the article" FILTERING ADULT IMAGE CONTENT WITH TOPIC MODELS" by Rudolf Hauke and Rainer Lienhart (Lienhart, R. and Hauke, R. 2009; Filtering adult image content with topic models; in *Proceedings of the* 2009 *IEEE international Conference on Multimedia and Expo* (New York, N.Y., USA, Jun. 28-Jul. 3, 2009); IEEE Press, Piscataway, N.J., 1472-1475.), which is incorporated herein by reference. Sexually explicit images are, for example, largely naked depictions of persons, depictions of primary or secondary sexual characteristics, and/or depictions of persons in sexually explicit positions. In order to enable such a classification, training with a plurality of exemplary images occurs first in the above-mentioned method of "probabilistic latent semantic analysis (PLSA)," so that there is a sufficient variety of characteristic image features with which new image material to be analyzed can be compared.

Alternatively or in addition, particularly film sequences with a plurality of single images can be classified as potentially illegal image material pi, i.e., as image material with a sexually explicit content, also based on depicted characteristic movement sequences of sexual acts by the persons shown in the image material, particularly based on such characteristic movement sequences of individual body regions of the depicted persons, and/or audio material, belonging to the film sequence, with sounds, noises, and language elements characteristic for sexual acts.

Image material in which no persons are shown or which have no sexually explicit depictions of persons is sorted out and a search is made for other image material to be analyzed in the data memory.

If the image material is classified as potentially illegal image material pi, it is to be assumed that sexually explicit images are present in the image material. Because it has not been established yet, however, whether the depicted persons are adults and thereby the image material is legal, or whether at least one underage person is depicted and the image material is therefore illegal, in a third process step S3 an age determination of the depicted persons is made in the image material classified as potentially illegal pi.

This age determination is made, for example, based on physical features, preferably based on the face of the particular person shown. Methods for age determination already known in the state of the art, but of course also methods to be developed in the future can be used for this. A known method, which can be used for age determination, is, for example, "probabilistic latent semantic analysis (PLSA)." Its use is described, for example, in the article "FILTERING ADULT IMAGE CONTENT WITH TOPIC MODELS" by Rudolf Hauke and Rainer Lienhart (Lienhart, R. and Hauke, R. 2009; Filtering adult image content with topic models; in *Proceedings of the* 2009 *IEEE international Conference on Multimedia and Expo* (New York, N.Y., USA, Jun. 28-Jul. 3, 2009); IEEE Press, Piscataway, N.J., 1472-1475. In this regard, training occurs with a very large number of comparison images of persons in a particular age group, so that accordingly persons depicted in new image material can be assigned to a specific age group with a very high probability of hits. Furthermore, the age determination can also be carried out, for example, by the method of "Facial Age Estimation by Nonlinear Aging Pattern Subspace," developed by Xin Geng, Kate Smith-Miles, and Zhi-Hua Zhou (Geng, X., Smith-Miles, K., and Zhou, Z. 2008; Facial age estimation by nonlinear aging pattern subspace; in *Proceeding of the* 16*th ACM international Conference on Multimedia* (Vancouver, British Columbia, Canada, Oct. 26-31, 2008), which is incorporated herein by reference. MM '08. ACM, New York, N.Y., 721-724. DOI=http://doi.acm.org/10.1145/1459359.1459469) or by the method of "BAYESIAN AGE ESTIMATION ON FACE IMAGES," developed by Chung-Chun Wang, Yi-Chueh Su, Chiou-Ting Hsu, Chia-Wen Lin, and H. Y. Mark Liao from the National Tsing Hua University, Institute of Information Science, Academic Sinica, Taiwan (Wang, C., Su, Y., Hsu, C., Lin, C., and Liao, H. Y. 2009, which is incorporated herein by reference; Bayesian age estimation on face images; in *Proceedings of the* 2009 *IEEE international Conference on Multimedia and Expo* (New York, N.Y., USA, Jun. 28-Jul. 3, 2009); IEEE Press, Piscataway, N.J., 282-285), which is incorporated herein by reference.

A thus determined age A of the depicted persons is compared with a predetermined age vA. The predetermined age vA can be predetermined advantageously by a user of the method, i.e., for example, by the particular law enforcement agencies, because the particular age at which an act or depiction is classified as sexual child abuse is different worldwide.

For example, in most countries sexual depictions of persons under the age of 12 are clearly classified as sexual child abuse or child pornography and prosecuted as a criminal offense. It is not sensible, however, to fixedly predetermine this age, because in a plurality of countries sexual depictions of persons over 12 years of age are also clearly classified as sexual child abuse and prosecuted as a criminal offense and by a fixed specification of such image material would not be found. Therefore, the possibility of specifying the age by a particular user of the method according to the particular requirements is especially advantageous.

If the determined age A of each person depicted in the image material exceeds the predetermined age vA, the image material is not classified as illegal image material, because sexually explicit depictions of persons as of a specific age of the depicted persons are not illegal. In other words, the image material is sorted out and a search is made for further image material to be evaluated in the data memory. If, however, at least one person whose determined age A is younger than the predetermined age vA is depicted in the potentially illegal image material pi, the image material is classified as illegal image material; i.e., the image material or what the image material depicts is child abuse or child pornography.

Because only depictions of real underage persons are evaluated as child abuse, it must be verified expediently at the latest at this time point of the method whether the image material represents real people or whether it is drawn image material or image material produced by special effects in some other manner or animated image material, for example, an animated film, a computer-generated animation film, or a so-called anime. Naturally also no biometric features of real persons can be detected or other features of a real crime site detected in such drawn image material or image material produced by special effects. Of course, this verification is also possible at any earlier time in the method starting with the finding of the image material in the data memory, in order to sort out at the outset image material that depicts no real persons. Image material depicting real persons is to be differentiated from such drawn image material or image material produced by special effects or animated image material based on its properties, because drawn image material or image material produced by special effects in some other manner or animated image material in contrast to image material depicting real persons in a real environment has no noise and no blurring due to camera shake and different color depths than image material of real persons and real backgrounds. This can be determined with suitable methods, for example, with methods for color analysis or color histogram analysis.

By the classification of the image material by means of a classification method, the additional age determination of the depicted persons, and the comparison with a predetermined age vA, the method is superior to methods, known from the state of the art, for evaluating image material and identifying image material that depicts child abuse. The method enables an effective automatic search for illegal image material, particularly also for new or modified image material, which would not be found by methods according to the state of the art, which work exclusively with an encoding of the image material, for example, using a cryptographic hash function and a comparison of the encoding. In this regard, because of the classification of the image material by a classification method and the additional age determination of the depicted persons, the method has a very high accuracy.

This enables in particular the efficient search in very large databases. A personal visual inspection of each individual image material found in the particular data memory is not necessary because of the automatic search and evaluation of the image material.

If the image material was classified as illegal image material, then it is determined in a fourth process step S4 for each depicted person whether the person is an offender or victim. This is carried out based on the already performed age determination of the depicted persons. Each depicted person whose determined age A is below the predetermined age vA is classified as a victim; each depicted person whose determined age A corresponds to the predetermined age vA or is above the predetermined age vA is classified as an offender.

After this, the biometric features of the persons depicted in the image material are detected; i.e., the biometric features of the depicted persons classified as offenders are detected in a fifth process step S5 and the biometric features of the depicted persons classified as victims in a sixth process step S6.

The determined biometric features of the depicted persons classified as offenders are compared in a seventh process step S7 with relevant databases, containing biometric features, for example, with offender databases of law enforcement agencies or police authorities. The determined biometric features of the depicted persons classified as victims in an eighth process step S8 are also compared with relevant databases for biometric features, for example, with victim databases of law enforcement agencies or police authorities or missing children databases. If the biometric features can be determined in an adequate quality and have already been stored in databases, this makes possible an automatic identification of the offenders and victims depicted in the image material.

Such databases for identifying offenders are, for example, databases of registered sex offenders or other available databases with biometric features, in the USA, for example, social services databases. Databases for identifying victims are, for example, missing children databases or databases with school year photos, because biometric features are also recognizable in such school photos. Further, searches for image material can be carried out by means of biometric features worldwide via the Internet, computer, and server in order to remove it.

For example, body size, fingerprints, facial geometry, hand vascular patterns, vein patterns, hand geometries, palm line patterns, nailbed patterns, ear shapes, voice, speech, lip movements, gait, a movement sequence, a skin characteristic, skin pore pattern, skin color, hair color, at least one sexual characteristic, dental status, at least one feature of at least one article of clothing, body modifications, and/or a feature of an iris and/or retina are detected as a biometric feature of the particular depicted person.

In so doing, preferably all biometric features detectable in the particular image material are used, extracted as a feature set, and compared with the relevant databases, whereby various known methods, for example, for fingerprint detection in single images and image sequences, and methods for facial recognition, voice recognition, iris recognition, and recognition of lip movements are available for detecting individual biometric features. Of course, however, methods developed in the future can also be used for this. Biometric features, for example, facial features or fingerprints, can be readily extracted especially in image sequences, i.e., in a film with a plurality of single images, in which persons are depicted, for example, from different perspectives. This also applies to three-dimensional depictions. For extracting a gait or a movement sequence, for example, the method can be used which is featured in the publication "Design and Implementation of People Tracking Algorithms for Visual Surveillance Applications" by Nils T. Siebel from the University of Reading, Computational Vision Group, Department of Computer Science, from March 2003, which is incorporated herein by reference.

The country or the part of the world from which the persons came can be determined, for example, by analyzing speech. Furthermore, analysis of speech and voice offers another possibility for age recognition of the depicted persons. The skin characteristics also include, for example, birthmarks, moles, scars, and other skin features or skin lesions. Such biometric features are often listed in databases, for example, in missing children databases or in databases for identifying offenders, so that a very good comparison and a good identification are possible. Body modifications are understood to be all voluntary or required visible changes on the body of the depicted persons, for example, scars, tattoos, piercings, transdermal implants, scarifications, or amputations. Furthermore, the dental status or dental condition of the depicted person can often be determined, such as, e.g., fillings, tooth gaps, or dental condition overall. Young individuals in particular have a characteristic dental condition, for example, because of primary teeth that are still present.

Furthermore, in a ninth process step S9, additional features present in the illegal image material are detected. In a tenth process step S10, the determined additional features are compared with relevant databases, for example, databases set up by law enforcement agencies for such features depicted in illegal image material, depending on the type of determined features, for example, with product databases or geographic databases.

Preferably information on a recording place and/or recording time of the image material is detected as an additional feature contained in illegal image material. Position data, which were determined by a recording device for recording the image material by means of a global positioning system and stored together with image data of the image material, are detected especially preferably as information on the recording place for the image material. For example, a plurality of recording devices, i.e., photo and video cameras, have a receiver for signals of the satellite-supported global positioning system, so that they constantly detect their current position and store it together with the image data. Crime sites of the depicted acts can be determined in this way in a simple and especially rapid manner, as a result of which the finding of the offenders and victims is made easier and further abuse can be prevented.

Furthermore, for example, sections of the surrounding area depicted in the image material, showing objects, windows, doors, particularly labeled products, and/or reflective surfaces and/or features of walls, floors, and/or ceilings are detected as additional features present in the illegal image material. This is used in identifying or at least localizing the shown crime site, for example, by identifying objects such as furniture or other objects or products, for example, based on recognizable logos or trademarks, which are not obtainable globally or not in the shown form, but only in certain parts of the world. This is also possible, for example, based on a wall, floor, or ceiling design, for example, based on characteristic wallpaper. The detection of these additional features can be carried out, for example, by means of the method "An Extended Set of Haar-like Features for Rapid Object Detection," developed by Rainer Lienhart and Jochen Maydt, Intel Labs, Intel Corporation, Santa Clara, Calif. 95052, USA (Rainer Lienhart and Jochen Maydt; An Extended Set of Haar-like Features for Rapid Object Detection; IEEE ICIP 2002, Vol. 1, pp. 900-903, September 2002), which is incorporated herein by reference.

Furthermore, the determined features can also be compared with features determined from other image material. If the crime site was already determined, for example, from other image material and has been identified, but the persons shown in the currently analyzed image material are not yet known, their identification is made easier by the knowledge of the crime site and its localization.

Shown crime sites can also be compared by the recognition of windows and doors. In addition, wider surroundings of the crime site and thereby also the crime site itself can be identified, for example, based on visible characteristic features of the surrounding area particularly through windows or through open doors, for example, characteristic buildings, or at least a region of the world where the crime site could be located can be narrowed down, for example, based on the weather situation, for example, snowfall, visible through windows or doors. This is possible, for example, by a comparison with databases of characteristic buildings or with geographic databases or meteorological databases. It is advantageous particularly for such meteorological databases when the time of recording the image material as well is detected, because a correlation of the date and weather provides further possible positional data of the crime site. When reflective, i.e., mirror-like surfaces are detected, for example, other characteristic features can be detected on these surfaces, for example, additional features of the surroundings and biometric features of persons reflected on the reflective surfaces.

If the illegal image material is a film comprising a plurality of single images, furthermore as an additional feature present in the illegal image material a plot can be detected. In this way, the image material can be compared with already known image material, in which the crime site, offender, and/or victim may already have been identified.

Advantageously, all detectable features depicted in the image material are detected and compared with as many databases as possible. Thus, for example, a detected additional feature enables an initial geographic localization and another feature a further approximation of an actual position of the crime site. Each individual additional feature when taken separately is perhaps less meaningful, yet the specific combination of depicted features is much more meaningful.

For example, a special product is detected which is only sold in Europe and the USA. Furthermore, a piece of furniture is detected which is sold in Europe and Africa but not in the USA. This limits the crime site to Europe. If buildings or landscape features are recognized, for example, through a window, or if, for example, the weather situation is determined and the time the image material was recorded is known, then the crime site can be limited relatively greatly to Europe or even localized precisely. Even if a precise localization of the crime site is not possible, but only a larger region in which the crime site is located, it is possible with justifiable effort and particularly reasonable financial costs and technical and personnel effort to mount a search for offenders and/or victims with involvement of the public in the particular region, for example, by publishing the face of the offender in media in the particular region. In this way, the likelihood of identifying and arresting the offenders and identifying the victims and ending their abuse is greatly increased and the technical, personnel, financial, and time resources necessary for this are greatly reduced.

The detection of the additional features in the image material is made possible, for example, by figure/background segmentation, also called foreground/background segmentation. For example, the method of "Eigenregions for Image Classification," developed by Clément Fredembach, Michael Schröder, and Sabine Süsstrunk, can be used for this (Fredembach, C, Schröder, M., and Susstrunk, S. 2004; Eigenregions for Image Classification; IEEE Trans. Pattern Anal. Mach. Intell. 26, 12 (December 2004), 1645-1649; DOI=http://dx.doi.org/10.1109/TPAMI.2004.123), which is incorporated herein by reference. The result of the segmentation is a clear separation of the persons shown in the image material from the background shown in the image material. The background can now be evaluated selectively and/or compared with databases as a whole or divided into background sections, for example, only individual objects, furniture, or a window and door arrangement and wallpaper, for example, with photo databases or databases from law enforcement agencies set up especially for this.

At present, for example, very many individuals store private photos, i.e., normal harmless photos, on servers in photo databases, in order to be able to show these that way over the Internet to other individuals, for example, friends, acquaintances, and relatives. If the background of the image material or background sections, for example, individual objects, pieces of furniture, windows, doors, or a combination thereof, i.e., a typical characteristic of a room shown in the illegal image material, is compared with these photos, then other photos of the room in which the sexual abuse had occurred or is still occurring can be found in such photo databases as well.

Because a registration is required in these photo databases, so that the person who uploaded the photos into the photo database is identifiable, the location shown in the photos can also be determined via this person.

The method of "probabilistic latent semantic analysis (PLSA)," known from the state of the art, for example, can be used for comparing the detected biometric features of the depicted persons or the detected additional features of the illegal image material with the relevant databases. Its use is described, for example, in the article "FILTERING ADULT IMAGE CONTENT WITH TOPIC MODELS" by Rudolf Hauke and Rainer Lienhart (Lienhart, R. and Hauke, R. 2009; Filtering adult image content with topic models; in *Proceedings of the* 2009 *IEEE international Conference on Multimedia and Expo* (New York, N.Y., USA, Jun. 28-Jul. 3, 2009); IEEE Press, Piscataway, N.J., 1472-1475). In so doing, the detected specific biometric or additional features in the image material, i.e., for example in photos of databases, are searched in that the photos in the databases are analyzed for these features and those photos are filtered out and indicated that also have the particular features. This allows for a rapid and automatic search of very large databases with a very high probability of hits.

Furthermore, for example, the method of "Distinctive Image Features from Scale-Invariant Keypoints," developed by David G. Lowe, Computer Science Department, University of British Columbia, Vancouver, B.C., Canada, presented in a publication of 5 Jan. 2004, can also be used for comparing the detected biometric or additional features (Lowe, D. G. 2004; Distinctive Image Features from Scale-Invariant Keypoints; Int. J. Comput. Vision 60, 2 (November 2004), 91-110. DOI=http://dx.doi.org/10.1023/B:VISI.0000029664.99615.94), which is incorporated herein by reference.

In addition, for example, the method of "Matching Local Self-Similarities across Images and Videos" developed by Eli Shechtman and Michal Irani at the Dept. of Computer Science and Applied Math, The Weizmann Institute of Science 76100 Rehovot, Israel, can be used (Shechtman, E., Irani, M. "Matching Local Self-Similarities across Images and Videos," Computer Vision and Pattern Recognition, 2007; CVPR '07. IEEE Conference on [Computer Vision and Pattern Recognition], vol., no., pp. 1-8, Jun. 17-22, 2007 doi: 10.1109/CVPR.2007.383198 URL: http://ieeexplore.ieee.org/stamp/stamp.jsp?tp=&arnumber=4270223&isnumber=4269956), which is incorporated herein by reference.

The identification of the victims and offenders and the identification of the crime site by determining other features in the image material makes it possible in particular to find victims and offenders and to stop the sexual abuse of children and the sexual abuse of other children by the offenders thereby. Physical and psychological injuries and disorders in the victims are prevented in this way, at least once they have been found. Apart from the destroyed or at least greatly disturbed life of the victims, considerable social and economic damage is also associated with such especially also psychological injuries and damage to the victims, which often persist for the entire life of the victims, because the victims often cannot pursue a normal life, i.e., a normal family life and a normal working life, and require intensive psychological care. Therefore, it is especially important to find the victims early to end the sexual abuse and further to find the offenders early to prevent sexual abuse of other victims from the start. The method makes a considerable contribution to this.

In a preferred embodiment, in another process step, not shown here, a unique identifier is generated for each found illegal image material. This unique identifier is, for example, a cryptographic hash function or some other identifier used to search for illegal image material with methods according to the state of the art. This type of identification of the image material occurs at present, for example, with an MD5 code or with an SHA-1 code. Expediently, the generated unique identifier is entered in at least one database, preferably in all existing databases with such identifiers. It is therefore important to use conventional identifiers according to the state of the art. Users of other methods searching for illegal image material based on such identifiers, can therefore use these identifiers and also find this new image material. This facilitates the work of law enforcement agencies.

In an embodiment of the method, in another process step not shown here, an age adjustment of the detected biometric features corresponding to at least one predetermined age is performed and determined age-adjusted biometric features are compared with relevant databases for biometric features. The age can be predetermined preferably by the user of the method. In this way, for example, offenders and victims can be identified who are depicted in the new image material and whose biometric data in the databases are already several years old, for example, children who have been missing for years. Some of the biometric data are subjected to changes due to the aging process, for example, body size.

If, for example, the date on which the image material was recorded is known, by age adjustment of the detected biometric features by a few years searches can be run in databases of missing children, who have already been missing for years, for example, with the age-adjusted biometric features, and victims can be identified in this way. This applies in a similar way to the identification of offenders, because the data material in many databases is often not current. However, because of the older age of the offenders, changes in biometric features are often minor here and relate, for example, to a change in hair color or to changes on a face, for example, an increase in wrinkles.

In another embodiment of the method, in another process step which is not shown here, in addition to the search for image material, the data memory is also searched for access data, for example, in files of electronic messages, i.e., email, or in text files. Found access data also enable and facilitate the search for image material in other data memories, which can be accessed by the owner of the particular end device or data memory. Moreover, by means of such access data, for example, access to file-sharing sites, chat rooms, and other platforms is made possible, where, for example, illegal image material is offered, traded, and/or exchanged or other illegal activities occur.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for automatically finding and digitally evaluating illegal image material, wherein a data memory is searched for image material, the method comprising:
   classifying, by a computer, found image material from the data memory that depicts image content that is potentially illegal image material;
   performing, by the computer, an age determination of the depicted persons in the image material classified as potentially illegal image material, and determining whether at least one person depicted in the image material classified as potentially illegal image material falls below a predetermined age;

after performing the age determination, detecting, by the computer, biometric features of the persons shown in the potentially illegal image material and comparing the detected biometric features with at least one database containing previously detected biometric features; and detecting, by the computer, at least one contained additional feature in the potentially illegal image material and comparing the at least one contained additional feature with at least one relevant database, wherein a personal visual inspection of the image material is not performed.

2. The method according to claim 1, wherein that the predetermined age is predetermined by a user of the method.

3. The method according to claim 1, wherein body size, at least one fingerprint, facial geometry, hand vascular pattern, vein pattern, hand geometry, palm line pattern, nailbed pattern, ear shape, voice, speech, at least one lip movement, gait, movement sequence, a skin characteristic, skin pore pattern, skin color, hair color, at least one sexual characteristic, dental status, at least one body modification, at least one feature of at least one article of clothing, and/or a feature of an iris and/or retina are detected as a biometric feature of the particular depicted person.

4. The method according to claim 1, wherein information on the recording location and/or recording time of the image material is detected as an additional feature contained in the illegal image material.

5. The method according to claim 4, wherein position data, which were determined by a recording device for recording the image material via a global positioning system and stored together with image data of the image material, are detected as information on the recording location for the image material.

6. The method according to claim 1, wherein at least one section of a surrounding area shown in the image material, at least one depicted object, at least one window, at least one door, at least one distinguishing feature of at least one depicted product, at least one painting, at least one poster, at least one clock, at least one reflective surface, and/or a characteristic of at least one wall, a floor, and/or a ceiling are detected as an additional feature contained in the illegal image material.

7. The method according to claim 1, wherein a plot is detected as an additional feature contained in the illegal image material, if the illegal image material is a film of a plurality of single images.

8. The method according to claim 1, wherein a unique identifier is generated for each found illegal image material.

9. The method according to claim 8, wherein a cryptographic hash function is generated as the unique identifier.

10. The method according to claim 8, wherein the generated unique identifier is entered in at least one database with such identifiers.

11. The method according to claim 1, wherein an age adjustment of the detected biometric features according to at least one predetermined age is carried out and the determined age-adjusted biometric features are compared with at least one database containing biometric features.

12. The method according to claim 1, wherein a permanently installed or mobile memory unit of a permanently installed or mobile computer, a database server, a mobile telephone, or some other permanently installed or mobile device are searched as a data memory.

13. The method according to claim 1, wherein data memory is searched for access data.

14. The method according to claim 1, wherein the method finds and digitally evaluates single images, films, and three-dimensional image material.

15. The method according to claim 1, wherein the classifying is performed by probabilistic latent semantic analysis (PLSA).

16. The method according to claim 1, wherein a film sequence with a plurality of single images based on depicted characteristic movement sequences of sexual acts by the persons shown in the image material, and audio material, belonging to the film sequence, with sounds, noises and language elements characteristic for sexual acts, are classifiable as the potentially illegal image material.

17. The method according to claim 1, wherein results of the age determination, the biometric features detection and the additional feature detection are utilized to determine an identity of the depicted persons in the potentially illegal image material.

* * * * *